(12) United States Patent
Bedor

(10) Patent No.: US 12,251,133 B2
(45) Date of Patent: Mar. 18, 2025

(54) VARIABLE-DIMENSION FIXATION ROD AND IMPLANTABLE STABILIZATION SYSTEM INCLUDING A VARIABLE-DIMENSION FIXATION ROD

(71) Applicant: SPINAL RESOURCES, INC., Fort Lauderdale, FL (US)

(72) Inventor: Bernard M. Bedor, Fort Lauderdale, FL (US)

(73) Assignee: SPINAL RESOURCES, INC., Fort Lauderdale, FL (US)

( * ) Notice: Subject to any disclaimer, the term of this patent is extended or adjusted under 35 U.S.C. 154(b) by 71 days.

(21) Appl. No.: 17/861,311

(22) Filed: Jul. 11, 2022

(65) Prior Publication Data

US 2022/0338904 A1     Oct. 27, 2022

Related U.S. Application Data

(63) Continuation of application No. 16/437,436, filed on Jun. 11, 2019, now Pat. No. 11,382,665.

(60) Provisional application No. 62/683,262, filed on Jun. 11, 2018.

(51) Int. Cl.
 *A61B 17/70* (2006.01)
(52) U.S. Cl.
 CPC ...... *A61B 17/7005* (2013.01); *A61B 17/7032* (2013.01)
(58) Field of Classification Search
 CPC ........................................... A61B 17/70–7046
 See application file for complete search history.

(56) References Cited

U.S. PATENT DOCUMENTS

| | | | |
|---|---|---|---|
| 5,024,213 A | | 6/1991 | Asher |
| 5,217,461 A | * | 6/1993 | Asher ................ A61B 17/7041 606/261 |
| 5,593,408 A | * | 1/1997 | Gayet ................ A61B 17/7055 606/261 |
| 5,601,554 A | | 2/1997 | Howland et al. |
| 6,102,912 A | | 8/2000 | Cazin et al. |
| 6,547,790 B2 | | 4/2003 | Harkey, III et al. |
| 7,794,476 B2 | | 9/2010 | Wisnewski |
| 7,806,913 B2 | | 10/2010 | Fanger et al. |
| 7,875,059 B2 | | 1/2011 | Patterson et al. |
| 7,967,847 B2 | | 6/2011 | Barker, Jr. et al. |

(Continued)

*Primary Examiner* — Eduardo C Robert
*Assistant Examiner* — Steven J Cotroneo
(74) *Attorney, Agent, or Firm* — McDonald Hopkins LLC

(57) ABSTRACT

An implantable, elongated fixation rod that, when coupled to a spinal column in a living patient, stabilizes a portion of the spinal column. The elongated fixation rod includes a plurality of different rod regions formed from surgical stainless steel that are aligned along a longitudinal axis of the elongated fixation rod. The different rod regions include different dimensions tailored to provide the different rod regions with different rigidities specific to support regions of the spinal column where the elongated fixation rod is to be installed. A smooth transition region at least 5 mm in length is integrally formed as part of a common monolithic structure with the different rod regions, and is devoid of a full, sharp step that forms a 90° angle relative to the longitudinal axis of the elongated fixation rod and separates the different rod regions along the longitudinal axis of the fixation rod.

33 Claims, 3 Drawing Sheets

(56) References Cited

U.S. PATENT DOCUMENTS

| | | | |
|---|---|---|---|
| 8,641,735 B2 * | 2/2014 | Serbousek | A61B 17/7004 606/259 |
| 8,657,856 B2 * | 2/2014 | Gephart | A61B 17/705 606/256 |
| 8,771,318 B2 | 7/2014 | Triplett et al. | |
| 9,289,243 B2 | 3/2016 | Dekutoski et al. | |
| 10,588,642 B2 | 3/2020 | Gauthier et al. | |
| 10,758,274 B1 | 9/2020 | Bess et al. | |
| 2003/0060824 A1 | 3/2003 | Viart et al. | |
| 2003/0191470 A1 | 4/2003 | Ritland | |
| 2005/0085815 A1 | 4/2005 | Harms et al. | |
| 2007/0049937 A1 | 3/2007 | Matthis et al. | |
| 2007/0191841 A1 | 8/2007 | Justis et al. | |
| 2007/0276380 A1 | 11/2007 | Jahng et al. | |
| 2009/0204156 A1 | 8/2009 | McClintock et al. | |
| 2010/0094302 A1 | 4/2010 | Pool et al. | |
| 2010/0114165 A1 * | 5/2010 | Ely | A61B 17/7004 606/264 |
| 2010/0114167 A1 | 5/2010 | Wilcox et al. | |
| 2012/0071928 A1 | 3/2012 | Jackson | |
| 2012/0116458 A1 | 5/2012 | Van Nortwick | |
| 2012/0290013 A1 * | 11/2012 | Simonson | A61B 17/7004 606/279 |
| 2013/0158606 A1 * | 6/2013 | Freudiger | A61B 17/7026 606/279 |
| 2014/0236239 A1 | 8/2014 | Biedermann et al. | |
| 2015/0157363 A1 | 6/2015 | Noordeen et al. | |
| 2015/0282842 A1 * | 10/2015 | Beyar | A61B 17/7049 606/273 |
| 2016/0106471 A1 | 4/2016 | Lynch | |
| 2017/0281237 A1 | 10/2017 | Murray | |
| 2018/0168694 A1 * | 6/2018 | Lee | A61B 17/7011 |
| 2019/0269438 A1 | 9/2019 | Simpson | |

* cited by examiner

VARIABLE-DIMENSION FIXATION ROD AND IMPLANTABLE STABILIZATION SYSTEM INCLUDING A VARIABLE-DIMENSION FIXATION ROD

CROSS-REFERENCE TO RELATED APPLICATIONS

This application is a continuation of U.S. Utility application Ser. No. 16/437,436 filed on Jun. 11, 2019 and titled "VARIABLE-DIMENSION FIXATION ROD AND IMPLANTABLE STABILIZATION SYSTEM INCLUDING A VARIABLE-DIMENSION FIXATION ROD," which claims priority to and the benefit from U.S. Provisional Application No. 62/683,262 filed on Jun. 11, 2018 and titled "VARIABLE-DIMENSION FIXATION ROD AND IMPLANTABLE STABILIZATION SYSTEM INCLUDING A VARIABLE-DIMENSION FIXATION ROD," the contents of which are incorporated by reference in their entireties.

FIELD OF THE INVENTION

This application relates generally to implantable systems including elongated structures with regions having different rigidity and, more specifically, to stabilization systems that use one or more fixation rods with gradual transitions between regions having a different cross-sectional dimension, and methods of using such stabilization systems to stabilize a segment of a spine of a living being.

DESCRIPTION OF RELATED ART

Conventional stabilization systems include rods that, when installed, stabilize and fix a spinal segment to treat various spinal conditions. The rods have a constant cross-sectional area along their entire length, and are chosen based on the cross-sectional area to provide the rigidity warranted by a specific application. However, the constant cross-sectional area of each rod constrains the surgeon during surgery by requiring the same cross-sectional area, and accordingly, the same rod stiffness or rigidity to be placed along the entire spinal segment to be stabilized.

Attempts have been made to develop a stabilizing system with rods of different cross-sectional areas. Such systems can employ multiple different rods coupled together in a linear arrangement. Each different rod can have a cross-sectional area along its entire length, chosen to support the specific spinal segment of interest. However, such stabilizing systems require the different rods to be manually coupled together with couplers or brackets. The use of such connecting structures introduces locations where the connection can weaken due to fatigue over time, requiring surgical intervention to correct. Further, the location of the fastener coupling the separate rods together must be taken into consideration when implanting the stabilizing system, and may interfere with placement of the stabilizing system.

BRIEF SUMMARY OF THE INVENTION

Accordingly, there is a need in the art for a stabilizing system including a fixation rod having a plurality of regions, each with a different cross-sectional area, diameter or other dimension. A transition region including a taper or other gradual transition can be formed as part of the transition rod, and extend between the regions having the different cross-sectional dimensions. The transition region can extend along a suitable length of the rod to make the transition between regions gradual enough that a screw can be secured to locations along each region, and also along the tapered region, using the same locking head.

According to one aspect, the subject application involves an implantable stabilization apparatus for stabilizing a portion of a skeletal structure of a living patient. The implantable stabilization apparatus includes an elongated fixation rod that includes: (i) a plurality of different rod regions that are aligned along a longitudinal axis of the fixation rod, and (ii) a transition region integrally formed as part of a common monolithic structure with the different rod regions. The different rod regions include different cross-sectional dimensions, and the transition region is tapered, separating the different rod regions along the longitudinal axis of the fixation rod. A fastener system couples the elongated fixation rod to the skeletal structure. The fastener system includes: (i) an anchor that is to be secured to the skeletal structure, (ii) a saddle coupled to the anchor, wherein the saddle is compatible to cooperate with a portion of at least one of the different rod regions, and (iii) a locking member that maintains cooperation between the saddle and the portion of at least one of the different rod regions, and interferes with separation of the fixation rod from the fastener system.

According to another aspect, the subject application involves a method of stabilizing a skeletal structure. The method includes installing a plurality of anchors on portions of the skeletal structure. An elongated fixation rod is secured to the plurality of anchors. The fixation rod includes a plurality of different rod regions having different cross-sectional dimensions that are aligned along a longitudinal axis of the fixation rod. A transition region is integrally formed as part of a common monolithic structure with the different rod regions. The transition region is tapered, and separates the different rod regions from each other along the longitudinal axis of the fixation rod. Joining the elongated fixation rod to the plurality of anchors comprises securing a portion of the transition region to a first anchor of the plurality of anchors, and securing a portion of at least one of the different rod regions to a second anchor of the plurality of anchors.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
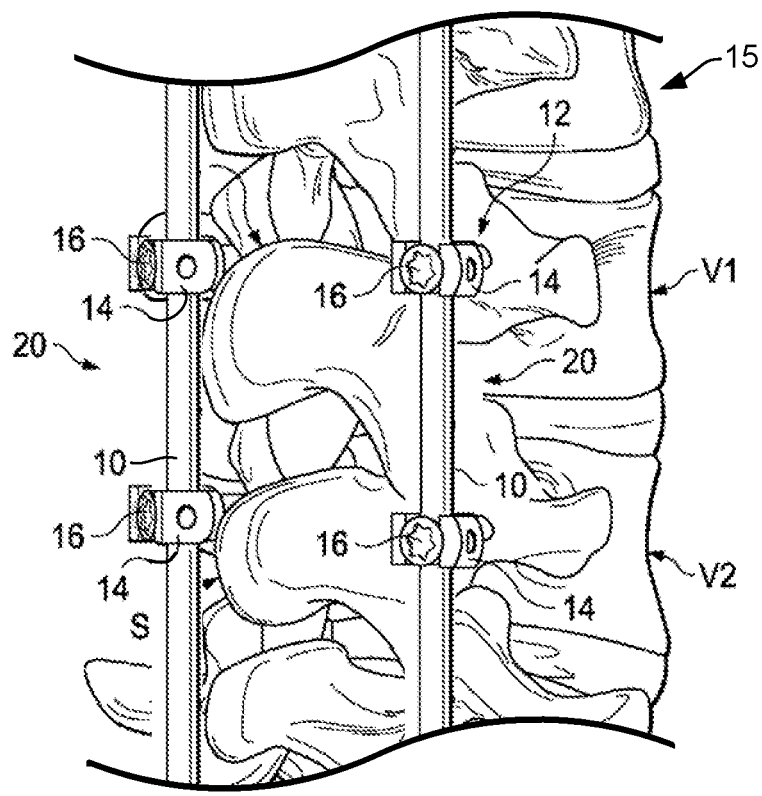
FIG. 1 is a perspective view of first and second stabilizing assemblies, each comprising a fixation rod having a plurality of regions with a different cross-sectional dimension attached to vertebral members according to one or more embodiments.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

Bone is a hard tissue that accumulates microscopic damage under conditions of normal physiological loading. This loading, in the form of walking down a flight of stairs, sneezing, bending over, etc. causes microscopic damage (microdamage). Unchecked, this microdamage is likely to accumulate over time. Fortunately, however, the body possesses the ability to repair microdamage through a process known as bone remodeling. Through this process, two types of cells remove damaged bone and replace it with new bone in a highly localized fashion (specifically, in the millimeter-scale region where microdamage is detected by the body). In addition to damage repair, the bone remodeling process also optimizes bone microarchitecture for maximum strength and minimum weight.

Bone cells also act to remove bone where no load is sensed in an effort to reduce overall weight of the bone. With the implantation of stiff metallic implants, much of the load around the anchor points (often orthopedic screws) is sustained by the implant itself, rather than the bone. Consequently, bone tends to atrophy around the implant. This re-distribution of load away from the bone to the implant that results in bone atrophy is commonly referred to in the bone community as stress shielding.

Stress shielding is a concern because it induces local removal of bone directly around the anchor points (often orthopedic screws). The gap between the surrounding bone surfaces and the screw leads to micro-motion. Micro-motion can result in localized bone damage which further induces bone removal (i.e. as a damage repair process). Stress shielding thus causes increased loading in the implant itself, which can exceed design tolerances. This reduces the life of the implant and often results in premature clinical fatigue failure. Fatigue failure is that which results from many load-unload cycles over time at levels below the maximum load tolerance of the implant. Subsequent revision orthopedic surgery is then required to replace the implant. One approach to reducing stress shielding is to reduce load sustained by the implant by reducing its rigidity, allowing it to flex and accommodate micro-motion of the structure to which the implant is anchored. The present stabilization system provides different, adequate anatomical support to separate regions of the patient, yet limits induction of bone atrophy.

With the implantation of rigid external fixators where intermediate vertebrae are fused together, increased loading occurs under normal physiological loading post-surgery. The increased loading experienced by the top and bottom-most vertebrae is due to the increased stiffness provided by the fixator. Flexible fixation can help to mitigate the sudden change in stiffness that results in such clinical fractures. It is believed that there is an opportunity to reduce the prevalence of fractures by providing patients with external spine fixation that is optimally tuned (e.g., with compatible rigidity) to the local spinal anatomy.

Bone structure and spinal musculature vary along the vertebral column. The rigidity of the inventive stabilization system varies as well to accommodate the local, patient-specific, anatomical stiffness. According to one embodiment, the stabilization system includes a fixation rod having a stepped design with linear regions having progressively smaller (or different) diameters or other cross-sectional dimension. However, the addition of steps on fixation rods can introduce highly localized stress concentrations. Stress concentrations exist because sharp features amplify local forces and can act as preferential sites of material failure, far below physiologically relevant loading. Stress concentrations in implanted devices reduce their life and can lead to premature failure. Accordingly, embodiments of the present fixation rod include smooth transition regions between each rod segment having a different diameter or other cross-sectional dimension. It is believed the transition regions mitigate stress concentrations that would otherwise be present at the sharp steps (e.g., formed at 90° or other such angle), while providing the fixation rod with continually variable stiffness along its length.

Furthermore, reducing the fixation rod's outer diameter, for example, results in improved fatigue performance. It is believed that this is due to the fact that peak material stresses occur at the outermost surfaces of a structure subjected to bending (such as that experienced during anterior or lateral bending of the spine). By reducing the diameter of the fixation rod in regions of high bending, the peak material stresses are also reduced, resulting in improved fatigue life.

With reference to the drawings, FIG. 1 shows first and second stabilization systems 20. Each stabilization system 20 includes a fixation rod 10 that has a plurality of linear regions D1, D2 (FIG. 2) with a different cross-sectional dimension attached to vertebral members V1, V2 by pedicle assemblies 12. Each pedicle assembly 12 includes a pedicle screw 14 and a retaining cap 16. To couple the fixation rod 10 to the vertebral members V1, V2, the pedicle screw 14 is threaded into an aperture formed in one of the vertebral members V1, V2. A saddle 17 (FIG. 2) of each pedicle assembly 12 receives a portion of the fixation rod 10. The saddle 17 can be formed as a generally U-shaped recess at a proximate end of the pedicle screw 14 that remains exposed externally of the bone while the pedicle screw 14 is installed in one of the vertebral members V1, V2. Threading 19 provided to a proximate end of the retaining cap 16 cooperates with threading 21 formed along an interior surface of the saddle 17 to exert a compressive force on the fixation rod 10, thereby securing the fixation rod 10 in the saddle 17.

The fixation rods 10 in FIG. 1 are positioned at a posterior side of the spine 15, on opposite sides of the spinous processes S. Fixation rods 10 may be attached to the spine 15 at any other location to be stabilized, such as lateral and anterior locations for example. The fixation rods 10 may also be attached at various sections of the spine, including the base of the skull and to vertebrae in the cervical, thoracic, lumbar, and sacral regions. Thus, the illustration in FIG. 1 is provided merely as a representative example of one application of a fixation rod 10.

In the exemplary assembly 20, the fixation rods 10 are secured to vertebral members V1, V2 by pedicle assemblies 12 comprising a pedicle screw 14 and a retaining cap 16. The outer surface of the fixation rod 10 is grasped, clamped, or otherwise secured between the pedicle screw 14 and retaining cap 16. In some embodiments, these are multi-axial pedicle screws. Other mechanisms for securing fixation rods 10 to vertebral members V1, V2 include hooks, cables, and other such devices. Further, examples of other types of retaining hardware include threaded caps, screws, and pins. The fixation rods 10 are also attached to plates in other configurations. In some examples, interbody devices or implants, fusion or dynamic, may be disposed between the adjacent vertebrae. Thus, the exemplary assemblies 20 shown in FIG. 1 are merely representative of one type of attachment mechanism.

Figure 2:
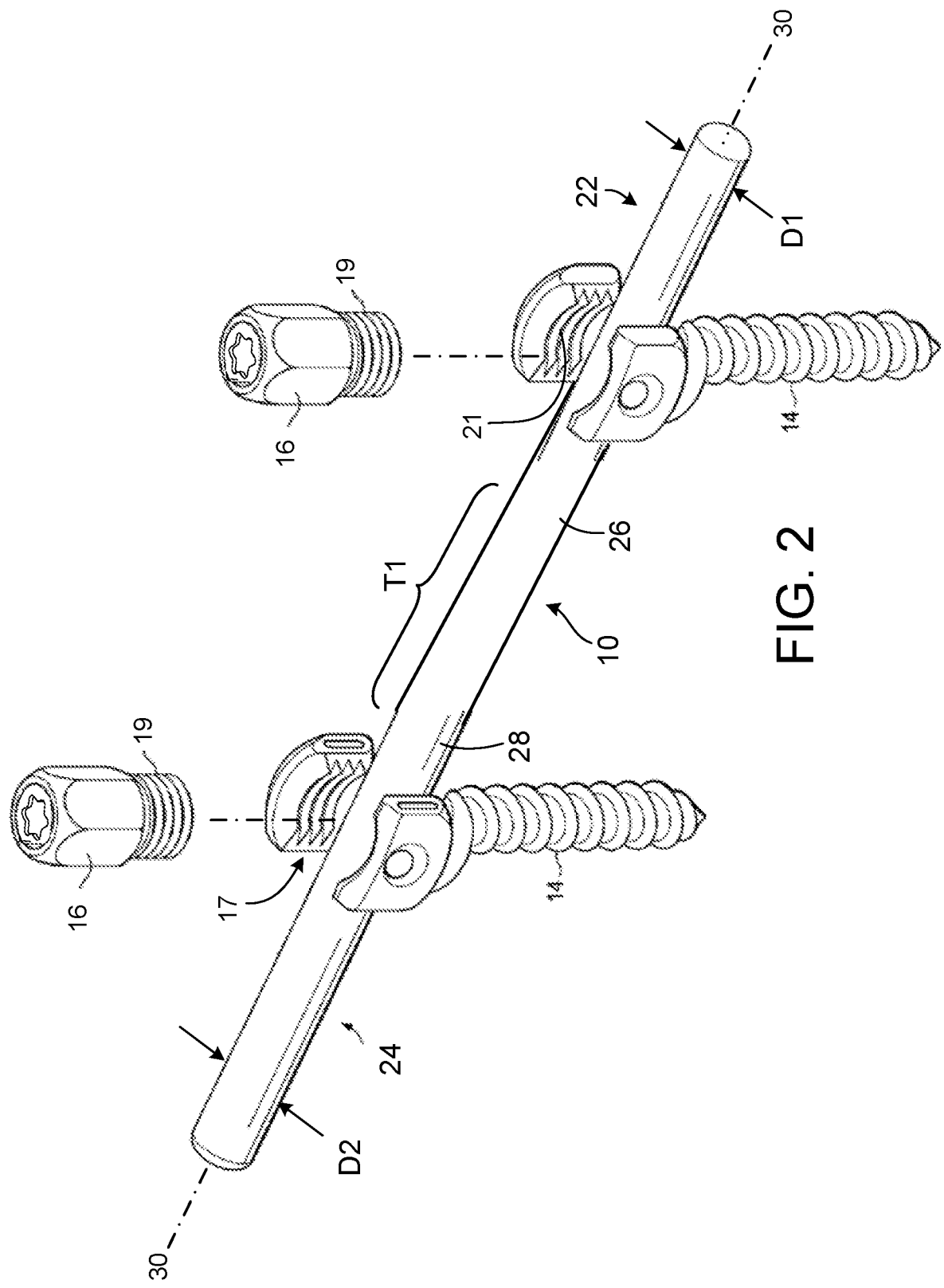
FIG. 2 is a perspective view of a fixation rod and a plurality of screws for anchoring a spinal implant to vertebral members.

As shown in FIG. 2, the fixation rod 10 includes a plurality of linearly-arranged rod regions 22, 24 separated by a transition region T1. The rod regions 21, 22 and the transition region T1 are integrally formed together as portions of the same monolithic structure, which can be substantially cylindrical in shape and have a generally circular or elliptical cross section. Embodiments of the fixation rod 10 are formed from surgical stainless steel, and can have any desired length to stabilize the region of the spine of interest. For example, the fixation rod 10 can have a length of up to 600 mm, up to 550 mm, up to 500 mm, up to 450 mm, up to 400 mm, up to 375 mm, up to 350 mm, etc. The fixation rod 10 is described herein as having a circular cross section for the sake of brevity and clarity, but other cross-sectional shapes can also be utilized to provide the fixation rod 10 with desired rigidity and other physical properties without departing from the scope of the present disclosure.

The circular cross section of the different regions 22, 24 can each have a different diameter D1, D2. The different diameters D1, D2 (or other dimension of the rod regions 22, 24 if the cross section is not circular) can be chosen to provide the respective regions with a desired rigidity to mitigate the effects of fatigue on the life of the implant due to movement of the respective spine segments. For example, the diameters D1, D2 can each be independently selected to be approximately 3.75 mm, 4.00 mm, 4.25 mm, 4.50 mm, 4.75 mm, 5.00 mm, 5.25 mm, 5.50 mm, 5.75 mm, any other diameter within a range from approximately 3.00 mm to about 6.00 mm, including any subrange therein. Examples of such subranges can be: up to 1.00 mm in size (e.g., D1 is approximately 4.50 mm and D2 is approximately 5.50 mm); up to 0.75 mm in size (e.g., D1 is approximately 4.50 mm and D2 is approximately 5.25 mm); up to 0.50 mm in size (e.g., D1 is approximately 4.50 mm and D2 is approximately 5.00 mm); etc. Having the approximate diameters above allows for machining tolerances of up to ±10%.

Despite the different diameters D1, D2 of the different rod regions 22, 24, embodiments of the present stabilization system 20 can include commonly-sized pedicle assemblies 12, or portions thereof, to couple the fixation rod 10 to the vertebral members V1, V2. For example, pedicle screws 14 having a common saddle 17 size and common retaining cap 16 size can be installed along each of the rod regions 22, 24. Thus, the saddle 17 and retaining cap 16 can be sized to accommodate the largest of the diameters D1, D2, but create a range of adjustment that is suitable to allow the retaining cap 16 to secure the smallest of the diameters D1, D2 within the saddle 17.

Forming different rod regions 22, 24 of the same fixation rod 10 with different diameters D1, D2 affords the different rod regions 22, 24 with different rigidity, tailored to the respective vertebral members V1, V2 to be stabilized by those rod regions 22, 24. To at least partially mitigate stress concentrations along the fixation rod 10, a transition region T1 forms a gradual transition between the different diameters D1, D2 of the rod regions 22, 24. Instead of a full, step change in the diameter at a point location along the length of the fixation rod 10, the transition region T1 elongates the portion of the fixation rod 10 over which the diameter changes from the diameter D1 to the diameter D2. For example, a first end 26 of the transition region T1 can have a diameter that is approximately the same as diameter D1, while a second end 28 of the transition region T1 can have a diameter that is approximately the same as diameter D2. The first and second ends 26, 28 of the transition region T1 can be separated from each other by at least 5 mm, at least 10 mm, at least 15 mm, at least 20 mm, at least 25 mm, at least 30 mm, at least 35 mm, at least 40 mm, etc. along a longitudinal axis 30 of the fixation rod 10.

Embodiments of the transition region T1 can be limited in length along the longitudinal axis 30 to less than a defined threshold such as 50 mm, for example, to allow the individual rod regions 22, 24 to have a substantially cylindrical shape. Thus, fixation rod 10 can be formed from a plurality of cylindrical rod regions 22, 24, and a tapered transition region, optionally giving the fixation rod 10 a stepped shape instead of a conical shape, with continuous angled sides along the entire length of the fixation rod 10.

Figures 3, 4:
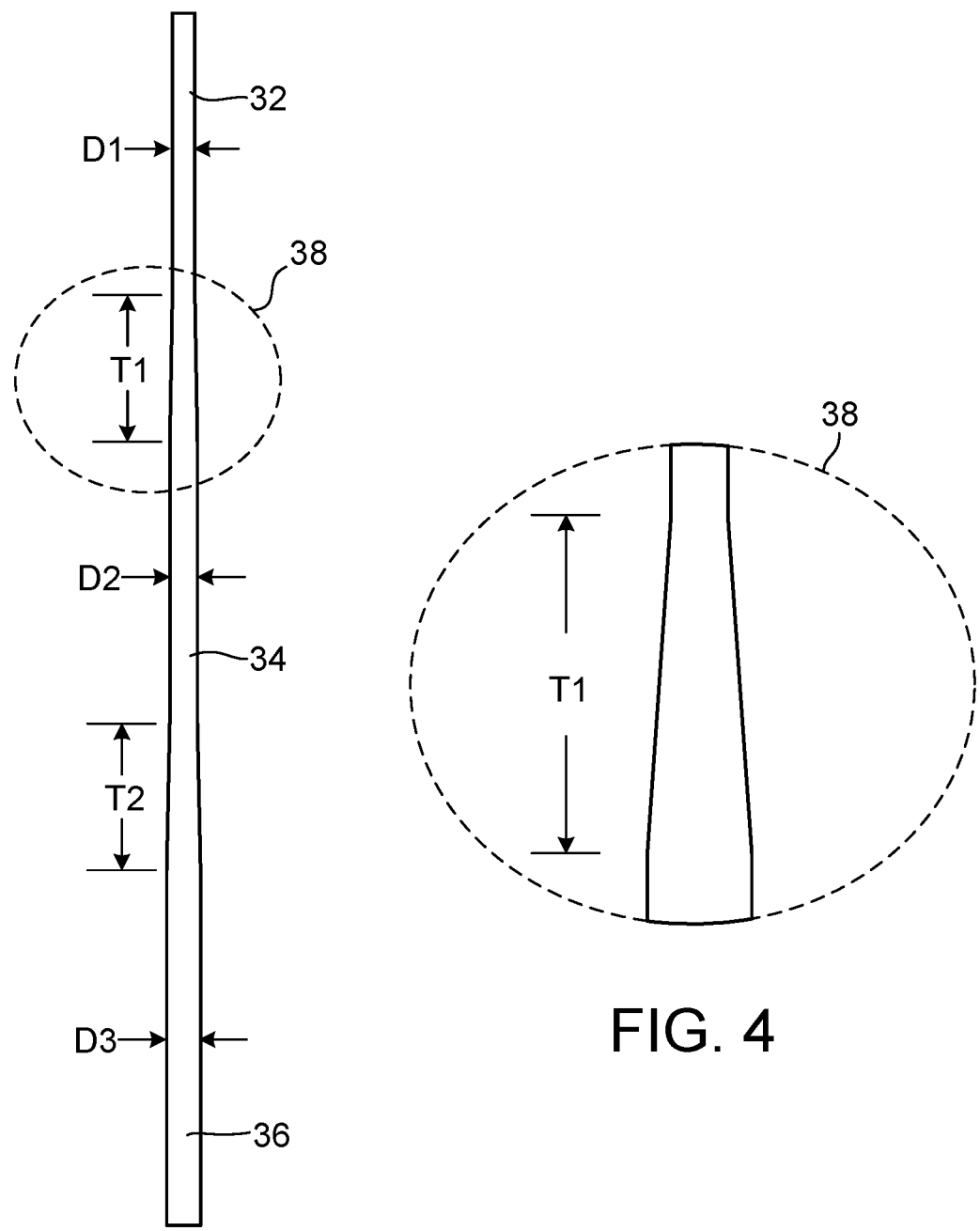
FIG. 3 is a top view of a fixation rod comprising three linear regions, each having a different diameter, and tapered transition regions separating the linear regions from each other.
FIG. 4 is an enlarged view of the transition region encircled by broken lines in FIG. 3.

The embodiment of the fixation rod 10 in FIG. 2 has two rod regions 22, 24 having different diameters D1, D2 separated by a transition region T1, however the present disclosure is not so limited. FIG. 3 shows another embodiment of the fixation rod 10 that includes three rod regions 32, 34, 36. Similar to the above embodiments, each rod region 32, 34, 36 can be cylindrical in shape with a substantially constant diameter D1, D2, D3 such as those described above. Transition regions T1, T2 separate the rod regions 32, 34, 36 from each other.

Because the difference in diameter between rod regions 32, 34, 36 is subtle, and may be difficult to discern from the drawings, FIG. 4 shows an enlarged view of the transition region T1 between the diameters D1, D2 enclosed by broken lines 38 in FIG. 3. The rate at which the diameter changes between diameters D1, D2 can optionally be constant across the length of the transition region T1. Thus, as shown in FIG. 4, the transition region T1 forms a substantially frustoconical shape between the rod regions 32, 34. The transition region T1 affords surgeons the flexibility to install the pedicle assemblies 12 at any location along the length of the fixation rod 10, including along the transition region T1 or at an intersection of the transition region T1 and one of the rod regions 32, 34.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system comprising an implantable elongated fixation rod and a pedicle assembly, the system comprising:
    first and second rod regions that are aligned along a longitudinal axis of the elongated fixation rod, the first and second rod regions each comprising different continuous cross-sectional dimensions configured to provide the first and second rod regions with different rigidities to provide structural support to specific regions of a spinal column where the elongated fixation rod is to be installed,
    at least one smooth and gradual transition region along the longitudinal axis integrally formed as part of a common monolithic structure with the first and second rod regions, wherein the transition region is tapered gradually between the different continuous cross-sectional dimensions of the first and second rod regions around an entirety of a perimeter of elongated fixation rod and separates the first and second rod regions along the longitudinal axis of the elongated fixation rod, wherein the at least one smooth and gradual transition region provides the elongated fixation rod with continually variable stiffness along the longitudinal axis of the elongated fixation rod;
    a first pedicle screw and retaining cap fixed to the first rod region; and
    a second pedicle screw and retaining cap fixed to the transition region.

2. The system of claim 1, wherein the different rod regions are linearly aligned along the longitudinal axis of the fixation rod.

3. The system of claim 1, wherein the at least one smooth and gradual transition region comprises an externally-exposed surface that is continuous with an externally-exposed surface of each of the different rod regions.

4. The system of claim 3, wherein an interface between the externally-exposed surface of at least one of the different rod regions and the externally-exposed surface of the transition region comprises an arcuate surface.

5. The system of claim 1, wherein the fixation rod comprises a second smooth and gradual transition region, wherein the smooth and gradual transition region and the second smooth and gradual transition region separate at least three different rod regions from each other.

6. The system of claim 1, wherein the at least one smooth and gradual transition region forms a frustoconical shape between the rod regions.

7. The system of claim 1, wherein the smooth and gradual transition region is at least 5 mm in length.

8. The system of claim 1, wherein the common monolithic structure is formed from surgical stainless steel.

9. The system of claim 1, wherein the different rod regions and the at least one smooth and gradual transition region collectively extend up to 600 mm in an axial direction along the longitudinal axis.

10. The system of claim 1 wherein a plurality of commonly sized pedicle assemblies are configured to be attached at any location along a length of the fixation rod.

11. The system of claim 1 wherein the monolithic structure is cylindrical in shape and includes circular or elliptical cross sections along its length.

12. The system of claim 1 wherein the monolithic structure includes a cross sectional shape that is not circular.

13. The system of claim 1, wherein the at least one smooth and gradual transition region is limited in length along the longitudinal axis to less than 50 mm.

14. The system of claim 1, wherein the first and second rod regions have a cylindrical shape.

15. The system of claim 1 further comprising a third pedicle screw and retaining cap fixed to the second rod region.

16. A system comprising an implantable, elongated fixation rod and a pedicle assembly, the system comprising:
    first and second rod regions aligned along a longitudinal axis, the first and second rod regions each comprising different continuous cross-sectional diameter tailored to provide the first and second rod regions with different rigidities configured to provide structural support to specific regions of a spinal column where the elongated fixation rod is to be installed;
    at least one smooth and gradual transition region positioned between the first and second rod regions along the longitudinal axis and integrally formed as part of a common monolithic structure with the first and second rod regions, wherein the transition region is tapered gradually between the different continuous cross-sectional diameters of the first and second rod regions around an entirety of a perimeter of elongated fixation rod, wherein the at least one smooth and gradual transition region provides the fixation rod with continually variable stiffness along the longitudinal axis;
    a first pedicle screw and retaining cap fixed to the first rod region; and
    a second pedicle screw and retaining cap fixed to the transition region.

17. The system of claim 16, wherein the different rod regions are linearly aligned along the longitudinal axis of the fixation rod and wherein the at least one smooth and gradual transition region comprises an externally-exposed surface that is continuous with an externally-exposed surface of each of the different rod regions.

18. The system of claim 17, wherein the different rod regions and the at least one smooth and gradual transition region collectively extend up to 600 mm in an axial direction along the longitudinal axis.

19. The system of claim 16, further comprising a second smooth and gradual transition region, wherein the smooth and gradual transition region and the second smooth and gradual transition region separate at least three different rod regions from each other.

20. The system of claim 16, wherein the at least one smooth and gradual transition region forms a frustoconical shape between the first and second rod regions.

21. The system of claim 16, wherein the first and second rod regions have a cylindrical shape.

22. The system of claim 16, further comprising a third pedicle screw and retaining cap fixed to the second rod region.

23. An implantable fixation rod and pedicle assembly comprising:
    first and second linearly arranged rod regions, wherein the first rod region comprises a first diameter and the second rod region comprises a second diameter, wherein the first diameter is different from the second diameter; and a transition region positioned between the first and second rod regions and monolithically formed with the first and second rod regions, wherein the transition region is tapered gradually between the first and second diameters at a constant rate around an entirety of a perimeter of elongated fixation rod, wherein the transition region provides a continually variable stiffness along a longitudinal axis of the first and second rod regions;

a first pedicle screw and retaining cap fixed to the first linearly arranged rod region; and a second pedicle screw and retaining cap fixed to the transition region.

24. The implantable fixation rod and pedicle assembly of claim 23, wherein the transition region is at least 5 mm in length.

25. The implantable fixation rod and pedicle assembly of claim 23, wherein the transition region is at least 10 mm in length.

26. The implantable fixation rod and pedicle assembly of claim 23, wherein the transition region is at least 15 mm in length.

27. The implantable fixation rod and pedicle assembly of claim 23, wherein the transition region is at least 20 mm in length.

28. The implantable fixation rod and pedicle assembly of claim 23, wherein the transition region is at least 25 mm in length.

29. The implantable fixation rod and pedicle assembly of claim 23, wherein the transition region is at least 30 mm in length.

30. The implantable fixation rod and pedicle assembly of claim 23, wherein the transition region is at least 35 mm in length.

31. The implantable fixation rod and pedicle assembly of claim 23, wherein the transition region is at least 40 mm in length.

32. The implantable fixation rod and pedicle assembly of claim 23, wherein the transition region is at least 50 mm in length.

33. The implantable fixation rod and pedicle assembly of claim 23 further comprising a third pedicle screw and retaining cap fixed to the second linearly arranged rod region.

* * * * *